United States Patent [19]

Wright

[11] 4,100,186

[45] Jul. 11, 1978

[54] ORGANIC NITRILES

[75] Inventor: Donald Wright, Middlesbrough, England

[73] Assignee: Imperial Chemical Industries Limited, London, England

[21] Appl. No.: 790,001

[22] Filed: Apr. 22, 1977

[30] Foreign Application Priority Data

May 24, 1976 [GB] United Kingdom ............... 21401/76

[51] Int. Cl.$^2$ ................... C07C 120/00; C07C 121/20
[52] U.S. Cl. ............................................. 260/465.8 D
[58] Field of Search ................................. 260/465.8 D

[56] References Cited

FOREIGN PATENT DOCUMENTS

| 1,385,883 | 12/1964 | France ........................ 260/465.8 D |
| 45-35,288 | 11/1970 | Japan ........................... 260/465.8 D |
| 1,177,182 | 1/1970 | United Kingdom ......... 260/465.8 D |

*Primary Examiner*—Joseph P. Brust
*Attorney, Agent, or Firm*—Cushman, Darby & Cushman

[57] ABSTRACT

Acrylonitrile is converted to a dimer product, at least 85% by weight of which consists of 1,4-dicyanobutenes, by reacting with an organic phosphite catalyst in a liquid solvent for the catalyst comprising an organic proton donor and substantially devoid of water, the acrylonitrile forming less than 50% by weight of the total liquid reaction mixture.

5 Claims, No Drawings

ORGANIC NITRILES

This invention relates to the manufacture of 1,4-dicyanobutenes from acrylonitrile.

It has already been proposed, for example in British Patent Specification No. 1,018,220, to dimerise acrylonitrile in the presence of an organic tertiary phosphine catalyst to give as the principal product 1,3-dicyanobutene-3, otherwise known as 2,4-dicyanobutene-1 or 2-methyleneglutaronitrile. There is a commercial demand, however, for 1,4-dicyanobutenes since these are directly convertible by successive hydrogenation into adiponitrile and hexamethylene diamine, but these 1,4-isomers are not reported as being obtained in major amount under normal conditions with the usual phosphine catalysts. British Patent Specification No. 1,051,821 has proposed to dimerise acrylonitrile using equally either organic phosphine or organic phosphite catalysts to give products said to be mixtures containing mainly 1,3-dicyanobutene-3 and 1,4-dicyanobutenes. Only one working example (Example 3) is given of the use of a phosphite catalyst and from the volatile product obtained only 1,3-dicyanobutene was isolated. In a development of the process (described in British Patent Specification No. 1,177,182), also said to apply equally to either organic phosphine or organic phosphite catalysts and in which certain hydrocarbon solvents are used and the product is worked up from a heavy phase formed in the reaction, the product is said to by mainly 1,3-dicyanobutene-3 with smaller amounts, for example up to 12% by weight, of 1,4-dicyanobutenes, although there are no working examples of the use of phosphite catalysts in the relevant specification.

Surprisingly in view of this prior art, we have now found that under selected conditions organic phosphite catalysts may be used to dimerise acrylonitrile to give major amounts of 1,4-dicyanobutenes.

Our invention provides a process for the conversion of acrylonitrile to a dimer product, at least 85% by weight of which consists of 1,4-dicyanobutenes, which process comprises reacting acrylonitrile with an organic phosphite catalyst in a liquid medium which is a solvent for the said catalyst, comprises an organic proton donor and is substantially devoid of water, the acrylonitrile forming less than 50% by weight of the total liquid reaction mixture.

The organic phosphites used as catalysts in the process of our invention are represented by the formula

in which R, R' and R" represent organic radicals which may be the same or different and two or more of which may be joined to each other. Preferably at least one of R, R' and R" represents an aliphatic or cycloaliphatic radical, especially an alkyl or cycloalkyl radical and especially an alkyl radical having from 1 to 6 and more preferably from 1 to 4 carbon atoms. They may also represent alkyl radicals carrying substituent groups especially alkoxy, aralkoxy, aryloxy, cyano, carbalkoxy and acyloxy, in which substituent groups the number of carbon atoms preferably does not exceed 10. More preferably at least two and still more preferably, all of R, R' and R" represent such aliphatic or cycloaliphatic radicals. Among suitable radicals which R, R' and R" may represent there may be mentioned methyl, ethyl, propyl, isopropyl, n-butyl, iso-butyl, t-butyl, amyl, hexyl, cyclopentyl, methylcyclopentyl, cyclohexyl, methylcyclohexyl, methoxyethyl, benzyloxyethyl, phenoxypropyl, cyanoethyl, carbomethoxyethyl and acetoxyethyl. Examples of suitable organic phosphites include trimethyl phosphite, triethyl phosphite tri-isopropyl phosphite, and diphenyl ether phosphite.

The liquid medium which contains the acrylonitrile to be dimerised and is a solvent for the organic phosphite catalyst comprises an organic proton donor and is substantially devoid of water. By substantially devoid of water we mean the the liquid medium contains less than 1 mole of water per mole of catalyst. Preferably the liquid medium contains less than 0.1 mole of water per mole of catalyst. In some cases it will be necessary or at least desirable to dry specially the acrylonitrile and the constituents of the liquid medium. The organic proton donor is preferably an alcohol especially an alcohol having up to 6 carbon atoms and more especially an alkanol having from 1 to 4 carbon atoms. Suitable organic proton donors include ethanol, isopropanol and t-butanol.

Apart from acrylonitrile, organic phosphite catalyst, and of course dimer product as formed, the liquid medium may consist solely of organic proton donor or may comprise other materials inert in the reaction. Thus the liquid medium may contain hydrocarbon solvents, such as aliphatic and cycloaliphatic hydrocarbons, for example pentane, hexane, heptane, cyclopentane, cyclohexane and methylcyclohexane, and aromatic hydrocarbons, for example benzene, toluene and xylene.

A preferred liquid medium comprises a mixture of organic proton donor and hydrocarbon solvent in the range of proportions by weight of 1:5 to 5:1, more preferably in the range 1:2 to 2:1.

The acrylonitrile forms less than 50% by weight of the total liquid reaction mixture. Preferably it forms less than 40% and may, for example, form as little as 5% of the said mixture. However, a preferred proportion of acrylonitrile is from 20% to 40% by weight of the total liquid reaction mixture.

The reaction is preferably carried out at temperature within the range 20° to 100° C. The reaction may be carried out under pressure but there is generally no advantage in using other than moderate pressure and pressure in the range 0.2 to 20 bar absolute are generally suitable.

The reaction period may vary widely depending in part on the degree of conversion of acrylonitrile which is aimed at, since it may be preferred to convert only a portion of the acrylonitrile and to recover and re-use unconverted material. Reaction periods may vary therefore from a few minutes, for example 3 mins, up to several hours, for example 20 hours. The process is readily adaptable to continuous operation.

The organic phosphite may form, for example, from 0.01% to 5% by weight of the total liquid reaction mixture.

After the reaction has progressed to the extent desired the dimer product may be isolated from the reaction mixture by any suitable means, for example other materials such as the organic proton donor and other solvent, if any, may be distilled off leaving the dimer product. The dimer product contains at least 85% by weight of 1,4-dicyanobutenes and may contain as much as 95% or more. The 1,4-dicyanobutenes may, if desired, be separated from other dicyanobutenes by fractional distillation, preferably under reduced pressure.

The invention is illustrated but not limited by the following examples.

EXAMPLES 1-10

The detailed results are contained in the following table. A mixture of acrylonitrile, an alcohol (as specified), an inert solvent (toluene) and an organic phosphite (as specified) was heated at the specified temperature for the specified time and product analysed for 1,4-dicyanobutenes and 2,4-dicyanobutene-1 (no other dimers were present in detectable amount.)

TABLE

| Expt. No. | Acrylonitrile g | Alcohol g | Toluene g | Phosphite g | Temp °C | Time hr | 1,4-dicyanobutene-1 g | 2,4-dicyanobutene-1 g | 1,4-dicyanobutene as 1% of total dimers |
|---|---|---|---|---|---|---|---|---|---|
| 1 | 6.54 | 0.67(a) | 10.7 | 0.77(c) | 80 | 3 | 1.3 | 0.03 | 97.7 |
| 2 | 8.2 | 3.85(a) | 8.7 | 0.7(c) | 80 | 3 | 0.93 | 0.015 | 98.4 |
| 3 | 8.0 | 8.0(b) | 8.6 | 0.26(c) | 60 | 4 | 0.44 | 0.016 | 96.4 |
| 4 | 8.0 | 6.0(b) | 8.6 | 0.25(d) | 80 | 0.5 | 0.59 | 0.022 | 96.4 |
| 5 | 8.0 | 6.0(b) | 8.6 | 0.25(d) | 60 | 3 | 0.5 | 0.015 | 97.1 |
| 6 | 8.0 | 6.0(b) | 8.6 | 0.25(d) | 80 | 0.5 | 0.33 | 0.010 | 97.2 |
| 7 | 8.7 | 2.6(b) | 8.25 | 0.3(d) | 60 | 3 | 0.57 | 0.016 | 97.2 |
| 8 | 8.3 | 0.95(b) | 9.1 | 0.28(d) | 60 | 3 | 0.28 | 0.011 | 96.2 |
| 9 | 7.9 | 7.8(e) | 8.7 | 0.32(d) | 80 | 3 | 0.98 | 0.050 | 95.1 |
| 10 | 9.3 | 5.72(b) | 9.3 | 0.15(f) | 80 | 3 | 0.24 | <0.010 | >96.0 |

NOTES:
(a) ethanol
(b) isopropanol
(c) triethyl phosphite
(d) tri-isopropyl phosphite
(e) t-butanol
(f) trimethyl phosphite

I claim:

1. A process for the conversion of acrylonitrile to a dimer product, at least 85% by weight of which consists of 1,4-dicyanobutenes, which process consists essentially of reacting acrylonitrile at a temperature of 20° to 100° C and a pressure of 0.2 to 20 bars (absolute) with, as sole catalyst, an organic phosphite of the general formula

in which each of R, R' and R" represents an alkyl radical having from 1 to 6 carbon atoms, in a liquid medium which is a solvent for the said catalyst, consists essentially of an alcohol having up to 6 carbon atoms as proton donor or of a mixture of said alcohol with a hydrocarbon solvent, and contains less than 1 mole of water per mole of catalyst, the acrylonitrile forming at least 5% but less than 50% by weight, and the said organic phosphite forming from 0.01% to 5% by weight of the total liquid reaction mixture.

2. The process of claim 1 in which the liquid medium contains less than 0.1 mole of water per mole of catalyst.

3. The process of claim 1 in which the hydrocarbon solvent is toluene.

4. The process of claim 1 in which the liquid medium comprises a mixture of organic proton donor and hydrocarbon solvent in the range of proportions by weight of 1:5 to 5:1.

5. The process of claim 1 in which the acrylonitrile forms 20% to 40% by weight of the total liquid reaction mixture.